(12) United States Patent
Yan et al.

(10) Patent No.: US 9,760,983 B2
(45) Date of Patent: Sep. 12, 2017

(54) SYSTEM AND METHOD FOR IMAGE REGISTRATION IN MEDICAL IMAGING SYSTEM

(71) Applicant: SHANGHAI UNITED IMAGING HEALTHCARE CO., LTD., Shanghai (CN)

(72) Inventors: Jichao Yan, Shanghai (CN); Qiang Li, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 15/448,750

(22) Filed: Mar. 3, 2017

(65) Prior Publication Data
US 2017/0178307 A1   Jun. 22, 2017

Related U.S. Application Data

(63) Continuation of application No. 15/314,055, filed as application No. PCT/CN2016/076358 on Mar. 15, 2016.

(30) Foreign Application Priority Data

Oct. 19, 2015   (CN) .......................... 2015 1 0679427

(51) Int. Cl.
*G06K 9/00*   (2006.01)
*G06T 5/50*   (2006.01)
(Continued)

(52) U.S. Cl.
CPC ................ *G06T 5/50* (2013.01); *A61B 90/36* (2016.02); *G06T 7/0012* (2013.01); *G06T 7/30* (2017.01);
(Continued)

(58) Field of Classification Search
CPC   G06T 5/50; G06T 7/30; G06T 7/0012; A61B 90/36
See application file for complete search history.

(56) References Cited

U.S. PATENT DOCUMENTS 7,162,066 B2   1/2007   Oosawa
8,224,046 B2   7/2012   Seghers et al.
(Continued)

FOREIGN PATENT DOCUMENTS

CN   102208109 A   10/2011
CN   103778626 A    5/2014
CN   104091337 A   10/2014

OTHER PUBLICATIONS

International Search Report for PCT/CN2016/076358 mailed on Jul. 8, 2016, 4 pages.
(Continued)

*Primary Examiner* — Kim Vu
*Assistant Examiner* — Molly Delaney
(74) *Attorney, Agent, or Firm* — Metis IP LLC

(57) ABSTRACT

The present disclosure relates to a system and method for image registration and image subtraction. The technique includes perform acquiring data related to the image processing, performing a pre-processing of the images, performing an image registration, performing an image subtraction, performing a post-processing of the images and managing storage of the data.

20 Claims, 15 Drawing Sheets

(51) Int. Cl.
  *G06T 7/00* (2017.01)
  *G06T 7/30* (2017.01)
  *A61B 90/00* (2016.01)

(52) U.S. Cl.
  CPC ... *A61B 2090/364* (2016.02); *A61B 2090/374* (2016.02); *A61B 2090/378* (2016.02); *A61B 2090/3762* (2016.02); *G06T 2207/10081* (2013.01); *G06T 2207/10088* (2013.01); *G06T 2207/10104* (2013.01); *G06T 2207/10108* (2013.01); *G06T 2207/10132* (2013.01); *G06T 2207/20224* (2013.01)

(56) References Cited

U.S. PATENT DOCUMENTS

| | | | |
|---|---|---|---|
| 8,929,624 B2 | 1/2015 | Knoplioch et al. | |
| 9,214,009 B2 | 12/2015 | Wan et al. | |
| 9,373,173 B2 | 6/2016 | Weistrand | |
| 2010/0232667 A1* | 9/2010 | Azar | A61B 5/055 382/131 |
| 2012/0121147 A1* | 5/2012 | Huang | G06T 7/136 382/131 |
| 2013/0182925 A1* | 7/2013 | Razeto | A61B 6/03 382/131 |
| 2016/0117797 A1 | 4/2016 | Li et al. | |
| 2016/0328852 A1* | 11/2016 | Beall | G06N 7/005 |
| 2016/0371862 A1* | 12/2016 | Silver | G06T 11/008 |

OTHER PUBLICATIONS

Written Opinion of the International Search Authority for PCT/CN2016/076358 mailed on Jul. 8, 2016, 4 pages.

\* cited by examiner

SYSTEM AND METHOD FOR IMAGE REGISTRATION IN MEDICAL IMAGING SYSTEM

CROSS-REFERENCE TO THE RELATED APPLICATIONS

This application is a Continuation of U.S. application Ser. No. 15/314,055, filed on Nov. 25, 2016, which is a U.S. national stage entry of International Application No. PCT/CN2016/076358 under 35 U.S.C. §371, filed on Mar. 15, 2016, designating the United States of America, which claims priority to Chinese Application No. 201510679427.3 filed on Oct. 19, 2015, the entire contents of which are hereby incorporated by reference.

TECHNICAL FIELD

The present disclosure generally relates to a system and method for image processing, and more particularly, a system and method for the detection of pathological changes from two or more medical images acquired at various times.

BACKGROUND

In medical image processing, the image registration may refer to the process of performing certain spatial transformation on an image, so as to facilitate comparisons of images of an object taken at different times or stages of a disease as it progresses. The image registration may be widely used for the purposes of medical diagnosis and treatment. The image registration may aid doctors in visualizing and monitoring pathological changes in an identical object over time. For example, the image registration may help doctors monitor the growth or shrinkage of a lesion or nodule and may aid in detecting subtle changes in the density of the lesion or nodule over time. Thus, it is desirable to improve the accuracy of image registration in medical images.

SUMMARY

The present disclosure provided herein relates to medical image processing. Specifically, the present disclosure relates to a system and method for generating temporal subtraction images. The generated temporal subtraction images may be obtained by performing a series of image registration on the images of an object taken at various times.

The images of an object taken at various stages may help doctors or radiologists to identify abnormalities and/or to determine changes which have occurred between two examinations. For example, the size and/or the location of a lesion at various stages of the object, as illustrated in the images, may be compared to indicate the development of the lesion. However, it may be difficult to compare images taken at various times. For instance, if the images were taken during the various breathing stages of the object, breathing may impact the images.

A method of image registration may be performed on the images so as to facilitate the comparison of different images taken at various times. To perform an image registration, at least two images may be provided. One image may be referred to the reference image. Another one may be referred to the floating image. A spatial transformation may be performed to deform the floating image to obtain an auxiliary image, and the difference between the auxiliary image and the reference image may be measured by a function, referred to as a cost function or an objective function. For a chosen cost function, an image registration method may utilize an optimization algorithm to reduce or substantially minimize the cost function based on the auxiliary image and the reference image, thus achieving an improved or optimal alignment between the reference image and the auxiliary image. A subtraction image may be obtained based on subtracting the reference image from the auxiliary image from the improvement or optimization. Using the subtraction image, the differences between the reference image and the floating image may be shown. The change at a region of interest may be demonstrated using the reference image, the floating image, and/or the subtraction image. If the floating image and the reference image are taken at different times, the subtraction image may indicate a change at a region of interest over time, and may be referred to as a temporal subtraction image.

Various ways of image registration may be designed by choosing a cost function, a spatial transformation to be performed on the image data, and/or an optimization algorithm.

In an aspect of the present disclosure, a method for image registration is provided. The method may include one or more of the following operations. A first image of an object may be designated as a reference image. The reference image may include at least a reference feature point and a reference structure. A second image of the object may be obtained. The second image may include a feature point and a structure. The feature point may correspond to the reference feature point of the reference image. The structure may correspond to the reference structure of the reference image. A first registration of the second image may be performed to obtain a first registered image. The first registration may include an affine transformation. The first registered image may include the feature point and the structure. A second registration of the first registered image may be performed to obtain a second registered image. The second registration may include aligning the structure in the first registered image with the reference structure in the reference image. The second registered image may include the feature point. A third registration of the second registered image may be performed to obtain a third registered image. The third registration may include aligning the feature point in the second registered image with the reference feature point in the reference image. The third registered image may be subtracted from the reference image to obtain a subtraction image. The subtraction image may include the feature point or the structure.

In another aspect of the present disclosure, a non-transitory computer readable storage medium including instructions is provided. The instructions, when executed by a processor, may cause the processor to effectuate a method including one or more of the following operations. A first image of an object may be designated as a reference image. The reference image may include at least a reference feature point and a reference structure. A second image of the object may be obtained. The second image may include a feature point and a structure. The feature point may correspond to the reference feature point of the reference image. The structure may correspond to the reference structure of the reference image. A first registration of the second image may be performed to obtain a first registered image. The first registration may include an affine transformation. The first registered image may include the feature point and the structure. A second registration of the first registered image may be performed to obtain a second registered image. The second registration may include aligning the structure in the first registered image with the reference structure in the reference image. The second registered image may include the feature point. A third registration of the second registered image may be performed to obtain a third registered image. The third registration may include aligning the feature point in the second registered image with the reference feature point in the reference image. The third registered image may be subtracted from the reference image to obtain a subtraction image. The subtraction image may include the feature point or the structure.

In some embodiments, the first registration may be based on the optimization of either mutual information or the mean squared error. In some embodiments, the optimization method of the first registration may be based on the downhill simplex method.

In some embodiments, the second registration may be based on the free form deformation model transformation. In some embodiments, the second registration may be based on the optimization of either mutual information or the mean squared error. In some embodiments, the second registration may be based on the L-BFGS method.

In some embodiments, the third registration may be based on the Demons model transformation. In some embodiments, the third registration may be based on the optimization of either mutual information or the mean squared error. In some embodiments, the third registration may be based on the L-BFGS method.

In some embodiments, the first image and the second image may be taken at different times.

In some embodiments, the first image, the second image, and the subtraction image may be displayed on a same display device. One or more of them may be displayed in a row or in a column.

In some embodiments, the reference feature point in the reference image and the feature point in the second image may be displayed in the subtraction image.

In some embodiments, the subtraction image may be fused with the reference image for displaying a change in the reference feature point and/or the reference structure between the reference image and the second image. Merely by way of example, a doctor may determine whether the reference feature point (e.g., a lesion) has changed by observing the difference between the reference feature point and the feature point. Such information may provide guidance for the doctor in diagnosis and/or to improve or revise a treatment plan.

In some embodiments, besides including a series of image registration, the method may further include identifying a structure in the second image within a region of interest in the subtraction image, and quantifying the pathological changes in the region of interest.

In a further aspect of the present disclosure, a system of image processing is provided. The system of image processing may include an acquisition module and an image processing module. The acquisition module may acquire a first image and a second image. The image processing module may designate the first image as a reference image. The image processing module may designate the second image as a floating image. The image processing module may perform image registration based on the reference image and the floating image, and perform image subtraction based on the image registration and the reference image to acquire a temporal subtraction image.

In some embodiments, the image processing module may include a post-processing unit to perform lesion detection and lesion measurement. In some embodiments, the image processing module may include a control unit to control the performance of a series of registrations.

In some embodiments, the imaging system may include a Computed Tomography (CT) system, a Digital Radiography (DR) system, a Computed Tomography-Positron Emission Tomography (CT-PET) system, a Computed Tomography-Magnetic Resonance Imaging (CT-MRI) system, an X-ray security system or an X-ray foreign matter detection system, or the like, or any combination thereof.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
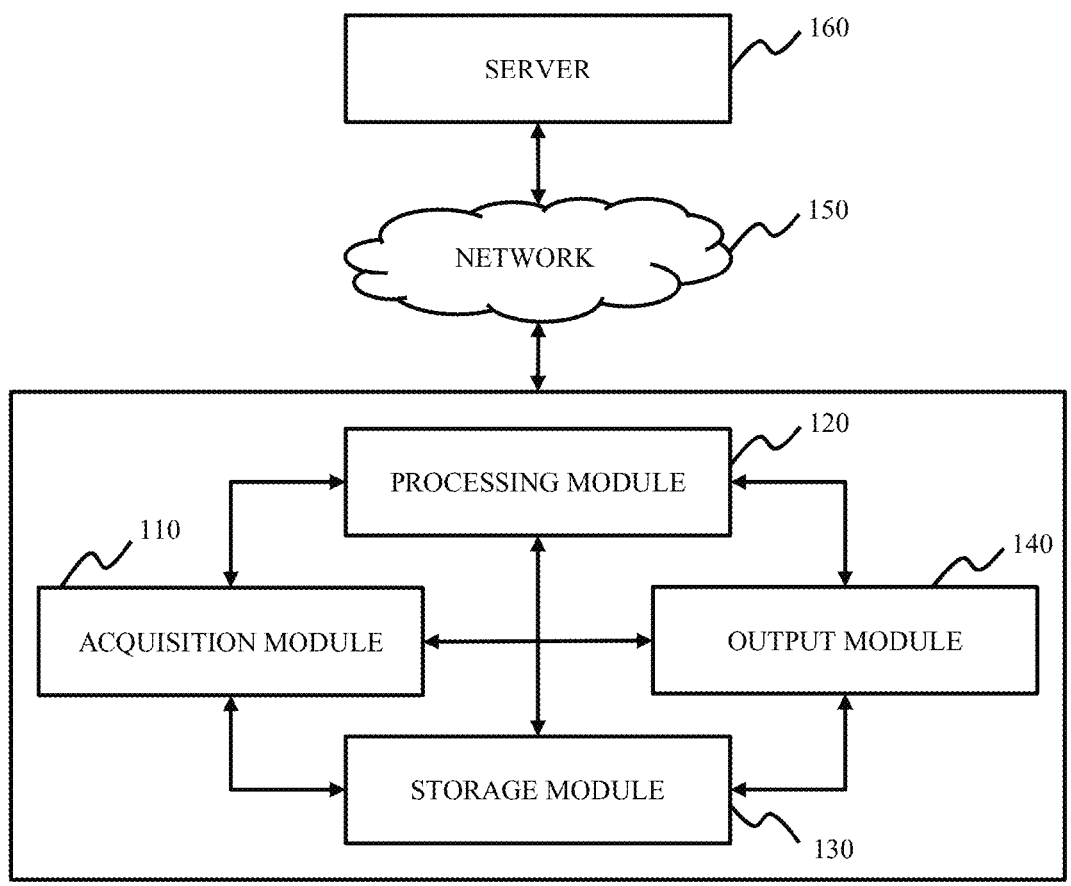
FIG. 1 shows an exemplary diagram of an image processing system according to some embodiments of the present disclosure.

In the following detailed description, numerous specific details are set forth by way of example in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof. It will be further understood that the terms "constructed" and "reconstruct", when used in this disclosure, may represent a similar process that an image may be transformed from data.

In some embodiments, the medical imaging system may be operated under various modalities, including but not limited to, Digital Subtraction Angiography (DSA), Magnetic Resonance Imaging (MRI), Magnetic Resonance Angiography (MRA), Computed tomography (CT), Digital Radiography (DR), Computed Tomography Angiography (CTA), Ultrasound Scanning (US), Positron Emission Tomography (PET), Single-Photon Emission Computerized Tomography (SPECT), CT-MR, CT-PET, CE-SPECT, DSA-MR, PET-MR, PET-US, SPECT-US, TMS (transcranial magnetic stimulation)-MR, US-CT, US-MR, X-ray-CT, X-ray-MR, X-ray-portal, X-ray-US, Video-CT, Vide-US, or the like, or any combination thereof. This is understood that the following descriptions are provided in connection with medical image processing for illustration purposes and not intended to limit the scope of the present disclosure. The image processing disclosed herein may be used for purposes other than medical treatment or diagnosis. For instance, the image processing may be used for purposes of detecting a fracture within a structure or its progression over time, a non-uniform portion within a piece of material, etc.

The radiation used by a medical imaging system may include a particle ray, a photon ray, or the like, or any combination thereof. The particle ray may include neutron, proton, electron, µ-meson, heavy ion, or the like, or any combination thereof. The photon beam may include X-ray, γ-ray, α-ray, β-ray, ultraviolet, laser, or the like, or any combination thereof. In some embodiments, the image registration may be the registration of a CT image. For example, various CT images obtained by scanning the lung area of a patient may be processed, or sometimes warped, to check the status of the lung area of the patient. In some embodiments, the image registration may be the registration of a DR image. For example, various DR images exhibiting the cerebral area of a patient over time may be warped and fused together for further processing.

In some embodiments, the object may be a human being, an animal, an organ, a texture, a region, a lesion, a tumor, or the like, or any combination thereof. Merely by way for example, the object may include a head, a breast, a lung, a trachea, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. In some embodiments, the medical image may include a 2D image and/or a 3D image. In some embodiments, the 3D image may include a series of 2D slices or 2D layers.

For illustration purposes, the following description is provided to help better understanding an image processing. It is understood that this is not intended to limit the scope of the present disclosure. For persons having ordinary skills in the art, a certain amount of variations, changes and/or modifications may be deducted under guidance of the present disclosure. However, those variations, changes and/or modifications do not depart from the scope of the present disclosure.

The present disclosure provided herein relates to medical image processing. Specifically, the present disclosure relates to a system and method for image registration. Image registration may be used in remote sensing, multispectral classification, environmental monitoring, image mosaicking, weather forecasting, creating super-resolution images. Image registration may also be widely sued in diagnosis and treatment of patient in medicine such as combining computer tomography (CT) and nuclear magnetic resonance (NMR) data to obtain more complete information about, for example, a patient, an object, weather, or the like, or a change thereof. Image registration may also be used in cartography (map updating), and in computer vision (target localization, automatic quality control). The process of image registration as illustrated in the present disclosure may be completely automated, to perform an automatic generation of the temporal subtraction images and/or fusion images. It may be embedded into a computer-aided and automated medical diagnosis and treatment system.

FIG. 1 shows an exemplary diagram of an image processing system according to some embodiments of the present disclosure. As described in FIG. 1, the image processing system may include an acquisition module 110, a processing module 120, a storage module 130, an output module 140, a network 150, and a server 160. The connection between different units may be wired or wireless. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), a Wi-Fi, a Wireless a Wide Area Network (WWAN), or the like, or any combination thereof.

The acquisition module 110 may acquire and/or send information related to image processing. The information may be acquired from the processing module 120, the storage module 130, the output module 140, the network 150 the server 160, or the like, or any combination thereof. The information may include data, such as a number, a text, an image, a voice, a force, a model, an algorithm, a software, a program, or the like, or any combination thereof. For example, the information may include information relating to an object, an operator, an instrument, an instruction, or the like, or any combination thereof. As used herein, the object may refer to a human being, an animal, an organ, a texture, a region, a lesion, a tumor, or the like, or any combination thereof. In some embodiments, the object may include a substance, a tissue, a specimen, a body, or the like, or any combination thereof. The object may include a head, a breast, a lung, a pleura, a mediastinum, an abdomen, a long intestine, a small intestine, a bladder, a gallbladder, a triple warmer, a pelvic cavity, a backbone, an extremity, a skeleton, a blood vessel, or the like, or any combination thereof. Exemplary information relating to an object may include ethnicity, citizenship, religion, gender, age, matrimony, height, weight, a medical history, job, personal habits, an organ or tissue to be examined, or the like, or any combination thereof. Exemplary information relating to an operator may include a department, a title, prior experience, credentials, an operating history, or the like, or any combination thereof, of the operator. Exemplary information relating to an instrument may include an operation status, the serial number of the medical imaging system, date of operation or the like, or any combination thereof, of the image processing system. Exemplary information relating to an instruction may include a control command, an operation command, such as a command for selecting an image, or the like, or any combination thereof, of the image processing system. Merely by way of example, the commands for selecting images may be an instruction to select one or more images in order to assess a change in images.

The processing module 120 may process different kinds of information received from different modules or units including the acquisition module 110, the storage module 130, the output module 140, the network 150, the server 160, or other modules or units that may generate information. The processing module 120 may process the data from the acquisition module 110 to generate a CT image of an object under examination.

The processing module 120 may perform pre-processing, image registration, image subtraction and post-processing, or the like, or any combination thereof. In some embodiments, the pre-processing may include image normalization, image segmentation, image reconstruction, image smoothing, suppressing, weakening and/or removing a detail, a mutation, a noise, or the like, or any combination thereof. In some embodiments, the image registration may include a series of registrations. In some embodiments, the post-processing may include a disease detection, a disease measurement, an image display, image storage management, other 2D and/or 3D post-processing technique, or the like, or any combination thereof. Merely by way of example, the images acquired after the image subtraction may contain noise, which may be treated in the post-processing.

The processing module 120 may transfer the information from the storage module 130 to a particular form that may be identified, understood, or executed by the processing module 120, and it may process the information from the acquisition module 110 to retrieve data from the storage module 130. The information from the acquisition module 110 to the output module 140 may be processed by the storage module 130 firstly so that it may be identified, understood, or executed by the processing module 120. The above description of the processing module 120 is merely for exemplary purposes, should not be understood as the only embodiments, and these examples do not limit the scope of the present disclosure.

In some embodiments, the processing module 120 may be a Central Processing Unit (CPU), an Application-Specific Integrated Circuit (ASIC), an Application-Specific Instruction-Set Processor (ASIP), a Graphics Processing Unit (GPU), a Physics Processing Unit (PPU), a Digital Signal Processor (DSP), a Field Programmable Gate Array (FPGA), a Programmable Logic Device (PLD), a Controller, a Microcontroller unit, a Processor, a Microprocessor, an ARM, or the like, or any combination thereof.

The storage module 130 may be store information related to image processing. In some embodiments, the storage module 130 may perform some storage-related function, such as data consolidation and/or data pre-processing. The storage module 130 may acquire information from or output to other modules. Merely by way of example, the storage module 130 may receive the data from the acquisition module, and then convey it to the processing module after possible pre-procession. The information stored in storage module 130 may be acquired from or output to external resource, such as a floppy disk, a hard disk, a CD-ROM, a network server, a cloud server, a wireless terminal, or the like, or any combination thereof.

The storage module 130 may store information by the way of electric, magnetic, optical energy, or virtual storage resources, etc. The storage module that store information by the way of electric energy may include Random Access Memory (RAM), Read Only Memory (ROM), flash memory, or the like, or any combination thereof. The storage module that stores information by the way of magnetic energy may include a hard disk, a floppy disk, a magnetic tape, a magnetic core memory, a bubble memory, a USB flash drive, or the like, or any combination thereof. The storage module that store information by the way of optical energy may include CD (Compact Disk), VCD (Video Compact Disk), or the like, or any combination thereof. The storage module that store information by the way of virtual storage resources may include cloud storage, a virtual private network, and/or other virtual storage resources. The method to store information may include sequential storage, link storage, hash storage, index storage, or the like, or any combination thereof.

The output module 140 may output the information and/or data related to image processing. For example, the output module 140 may display the images acquired from the acquisition module 110 and/or the storage module 130, the output module 140 may display and/or output an image processed by the processing module 120. The output module 140 may include or be communicated with a personal computer, a desktop computer, a personal digital assistant, a somatosensory device, a mobile phone, a screen, a monitor, a printer, or the like, or any combination thereof. The output module 140 may be connected with one or more external devices. The external devices may include a mouse, a keyboard, a remote-control unit, a sensor, or the like, or any combination thereof.

The network 150 may establish connection between any two of the acquisition module 110, the processing module 120, the storage module 130, the output module 140, and the server 160 to communicate with each other. The network 150 may be a single network or a combination of different networks. For example, the network 150 may be a local area network (LAN), a wide area network (WAN), a public network, a private network, a proprietary network, a Public Telephone Switched Network (PSTN), the Internet, a wireless network, a virtual network, or the like, or any combination thereof.

The server 160 may store and/or implement some information related to image processing and some image processing algorithms. The server 160 may be a cloud server. Merely by way of example, the server 160 may be implemented in a cloud server that may provide storage capacity, computation capacity, or the like, or a combination thereof.

It should be noted that the above descriptions about the image processing system is merely an example, should not be understood as the only embodiment. Obviously, to those skilled in the art, after understanding the basic principles of the connection between different modules, the modules and connection between the modules may be modified or varied without departing from the principles. The modifications and variations are still within the scope of the current disclosure described above. In some embodiments, these modules may be independent, and in some embodiments, part of the modules may be integrated into one module to work together. Merely by way of example, some information may be stored in the server 160, some steps of image processing may be performed by the server 160, functions of the acquisition module 110 and the output module 130 may be performed in one module, the information received by the acquisition module 110 may be from the server 160.

Figure 2:
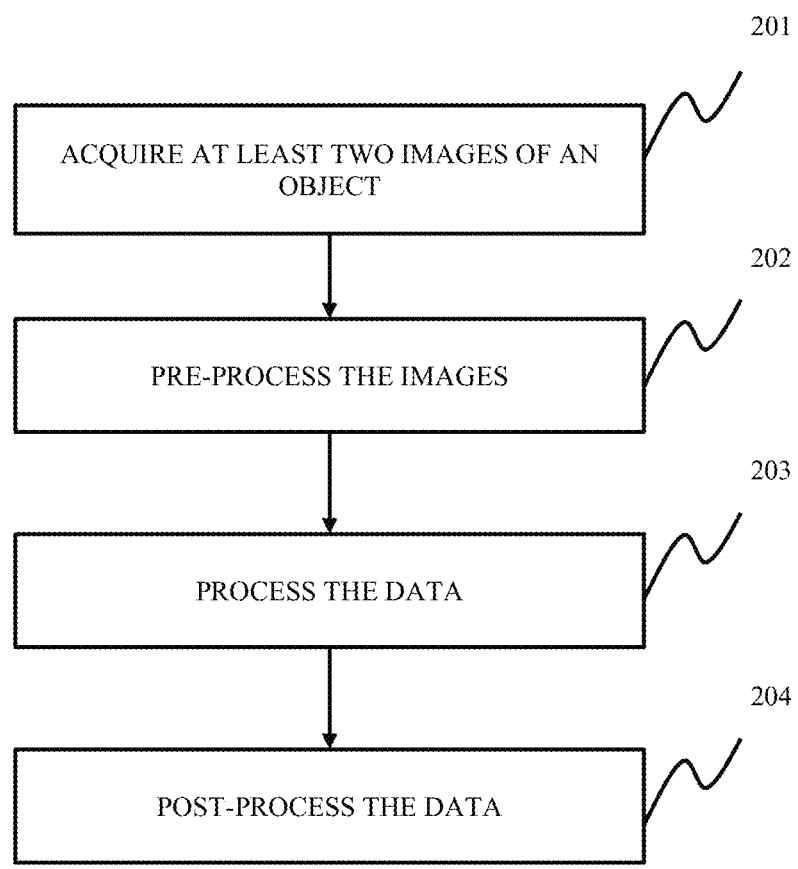
FIG. 2 illustrates an exemplary flowchart of image processing according to some embodiments of the present disclosure.

FIG. 2 illustrates an exemplary flowchart of image processing according to some embodiments of the present disclosure. In step 201, at least two images of an object may be acquired. The images may be obtained via the acquisition module 110. The images may be generated at different times. For example, at least one image may be generated at the early stage of lung cancer of an object, and at least one image may be generated at a late stage of lung cancer of the same object. The two images may be a mono-modality image. The images may be acquired by the same mono-modality imaging device or the same multimodality imaging devices. The images may be acquired by different mono-modality imaging device. For instance, the images may be generated by Digital Subtraction Angiography (DSA), Magnetic Resonance Imaging (MRI), Magnetic Resonance Angiography (MRA), Computed tomography (CT), Digital Radiography (DR), Computed Tomography Angiography (CTA), Ultrasound Scanning (US), Positron Emission Tomography (PET), Single-Photon Emission Computerized Tomography (SPECT), CT-MR, CT-PET, CE-SPECT, DSA-MR, PET-MR, PET-US, SPECT-US, TMS (transcranial magnetic stimulation)-MR, US-CT, US-MR, X-ray-CT, X-ray-MR, X-ray-portal, X-ray-US, Video-CT, Vide-US, or the like, or any combination thereof. In some embodiments, the images may be two CT images of an object generated at different times and/or at different hospitals. Merely by way of example, the images may include two DR images of an object taken at different times and/or different hospitals using different imaging devices. The imaging devices may be of the same type or different types. One image may be set as a reference image. As used herein, a reference image may refer to an image taken at an early time point. For example, the reference image may be an image of the object at an initial stage of lung cancer at an early time, showing the status of the object and the distribution of the lesion or nodule within a lung area. As used herein, a floating image, or a dynamic image, may refer to an image of a same or similar area as the reference image. A floating image may be taken at a different time than the reference image. For instance, a floating image of the object may show the status of the same or similar lung area of the object at a later time, such as the distribution or density of the lesion or nodule within the lung area.

In step 202, the two images of the object may be subject to pre-processing. The pre-processing procedure may be performed by the acquisition module 110. Alternatively, the pre-processing procedure may be performed by the processing module 120. In some embodiments, the pre-processing may include a way of identification of rib area in a medical image. For example, a medical image exhibiting the lung area may be obtained first. For example, a method in the Chinese Application No. 201310170102.3 was disclosed to segment the lung area out of the image. A pre-processing may be performed on the medical image to locate the rib(s) within the lung area in the image. The pre-processing may be performed based on a Hough template. The Hough template may be utilized to perform the Hough transformation on the lower boundary part of the ribs within the lung area. Based on the value of the gravity center of the Hough template, a substantially optimal Hough template may be determined. The lower boundary part of the ribs corresponding to the substantially optimal Hough template may be distilled, and made smooth to be used as a baseline template for the image. Using the baseline template, a generalized Hough transformation may be performed at the lower boundary part of the rib(s) within the lung area to furnish an initial positioning. A bi-lateral dynamic programming algorithm may then be performed to segment the upper and lower boundary of the ribs, and transfer the result of segmentation backward to the image, so as to separate the rib(s) within the lung area. In some embodiments, the pre-processing may include image normalization, image segmentation, image recognition, image reconstruction, image smoothing, suppressing, weakening and/or removing a detail, a noise, or the like, or any combination thereof.

Image segmentation may refer to the process of partitioning a digital image into multiple segments. In some embodiments, the method of a segmentation may include a threshold segmentation, a region growing segmentation, a region split and/or merge segmentation, an edge tracing segmentation, a statistical pattern recognition, a C-means clustering segmentation, a deformable model segmentation, a graph search segmentation, a neural network segmentation, a geodesic minimal path segmentation, a target tracking segmentation, an atlas-based segmentation, a rule-based segmentation, a coupled surface segmentation, a model-based segmentation, a deformable organism segmentation, or the like, or any combination thereof. In some embodiments, the segmentation method may be performed in a manual mode, a semi-automatic mode, or an automatic mode. The three modes may allow a user or an operator to control the image processing in various degrees. In some embodiments of the manual mode, a parameter of the segmentation may be determined by the user or the operator. Exemplary parameters may include a threshold level, a homogeneity criterion, a function, an equation, an algorithm, a model, or the like, or any combination thereof. In some embodiments of the automatic mode, the segmentation may be incorporated with some information about a desired object including, e.g., a priori information, an optimized method, an expert-defined rule, a model, or the like, or any combination thereof. The information may also be updated by training or self-learning. In some embodiments of the semi-automatic mode, the user or the operator may supervise the segmentation process to a certain extent.

Image smoothing may refer to a process of removing noise digitally and improve the quality of an image. The processing of image smoothing may be in a spatial domain and/or a frequency domain. In some embodiments, smoothing in the spatial domain may include processing image pixels and/or voxels directly. Smoothing in the frequency domain may include processing a transformation value firstly acquired from the image and then inversely transform the transformation value into a spatial domain. Exemplary image smoothing may include a median smoothing, a Gaussian smoothing, a mean smoothing, a normalized smoothing, a bilateral smoothing, or the like, or any combination thereof.

In step 203, a series of image registration may be performed on the floating image to obtain one or more desired target images for comparison with the reference image. In some embodiment, a series of coarse registration, fine registration, and super-fine registration may be performed sequentially on the floating image, or an image resulted therefrom (e.g., an auxiliary image described elsewhere in the present disclosure. An image registration may include choice of a group of spatial transformations, a designation of a cost function, and an optimization method. The group of spatial transformations may describe specific spatial transformations that may be performed on the floating images. In some embodiment, the group of spatial transformations may be a group of translations. In some embodiments, the group of spatial transformations may be a group of rigid motions. In some embodiments, the group of spatial transformations may be a group of affine transformations. The group of spatial transformation may also be based on an elastic model or a fluid model.

A cost function may be used to measure the difference between two images. In some embodiments, the cost function may be mutual information (MI) or relative entropy between the two images. Based on information theory, mutual information may represent the amount of information that one image may contain about a second image. Mutual information may be maximized by aligning the two images in an optimal way. For illustration purposes, mutual information between a first image A and a second image B may be expressed as Equation (1) below:

$$C_{similarity}(A,B)=H(A)+H(B)-H(A,B), \quad (1)$$

wherein H(A) and H(B) may denote the marginal entropies of A, B, and H(A, B) may denote their joint entropy calculated from the joint histogram of A and B.

In some embodiments, the cost function may be normalized mutual information (NMI) between the two images. The normalized mutual information may be computed using the image entropies according to Equation (2):

$$C_{similarity}(A, B) = \frac{H(A) + H(B)}{H(A, B)}, \quad (2)$$

wherein H(A) and H(B) may denote the marginal entropies of A, B, and H(A, B) may denote their joint entropy calculated from the joint histogram of A and B.

In some embodiments, the cost function may be given as a mean squared error (MSE) between the two images. In some embodiments, the cross correlation between the two images may be designated as the cost function. In some embodiments, the cost function may be given as a sum of squared intensity differences between the two images.

It should be noted that the above description of the cost function is provided for the purposes of illustration, not intended to limit the scope of the present disclosure. For persons having ordinary skills in the art, various variations and modifications may be conducted under the teaching of the present disclosure. However, those variations and modifications may not depart the protecting scope of the present disclosure. For example, the cost function may be Hybrid-NMI.

In step 203, an optimization method may be selected based on the nature of the cost function and the group of spatial transformations selected. In some embodiments, the optimization of a cost function may involve a plurality of parameters. For example, for a free-form deformation (FFD) algorithm based on the B-spline, with the control nodes of 10×10×10, the parameters for describing the degree of freedom may reach up to 13×13×13=2197. The complexity of optimization may depend on the size of mesh, i.e. the distance between the control nodes, because a small mesh size may involve a great amount of computation. The optimization method may include a Powell method, a downhill simplex method, a gradient descent method, a downhill simplex method, a deepest gradient descending method, a conjugate gradient method, a pseudo-Newton method, a quasi-Newton method, a least-squares and Gauss-Newton method, a Broyden-Fletcher-Goldfarb-Shannon (BFGS) method, a limited-memory Broyden-Fletcher-Goldfarb-Shannon (L-BFGS) method, a simulated annealing method, an ant colony optimization (ACO) method, a genetics algorithm (GA), a Levenberg-Marquardt optimization method, a geometric hashing method, a particle swarm optimization (PSO) method, a firefly algorithm (FA) method, or the like, or a combination thereof.

In step 204, the post-processing may be performed. In some embodiments, a procedure of post-processing may be performed on the result images from step 203. A subtraction image may be generated by subtracting a floating image, or an image relating to the floating image (e.g., an auxiliary image described elsewhere in the present disclosure), from a reference image. In some embodiments, the floating image may include a same or similar region as the reference image. In some embodiments, the floating image may be taken at a different time. The subtraction image obtained by way of subtracting a floating image taken at a different time than the reference image may be referred to as a temporal subtraction image. The temporal subtraction image may show the differences between the transformed image and the reference image. In some embodiments, the subtraction image (e.g., a temporal subtraction image) may be combined with the reference image to provide a fused image. The fused image, and/or the reference image, as well as other relevant images (e.g., one or more floating images), may be further processed to designate a region of interest. The size of the region of interest may be calculated, and the location of the region of interest may be labelled for future use. In some embodiments, the temporal subtraction image and/or the fused image may be provided to a display device for display. The post-processing may include a disease detection, a disease measurement, an image display, image storage management, other 2D and/or 3D post-processing technique, or the like, or any combination thereof. Merely by way of example, the images acquired after the image subtraction may contain noise, which may be treated in the post-processing.

It should be noted that the flowchart described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure. For example, step 201, step 202, step 203 and step 204 may be performed sequentially at an order other than that described above in FIG. 2. At least two steps of step 201, step 202, step 203 and step 204 may be performed concurrently. Step 201, step 202, step 203 and step 204 may be merged into a single step or divided into a number of steps. In addition, one or more other operations may be performed before/after or in performing step 201, step 202, step 203, and step 204. At least one of step 201, step 202, step 203 and step 204 may be unnecessary and may be omitted.

Figure 3:
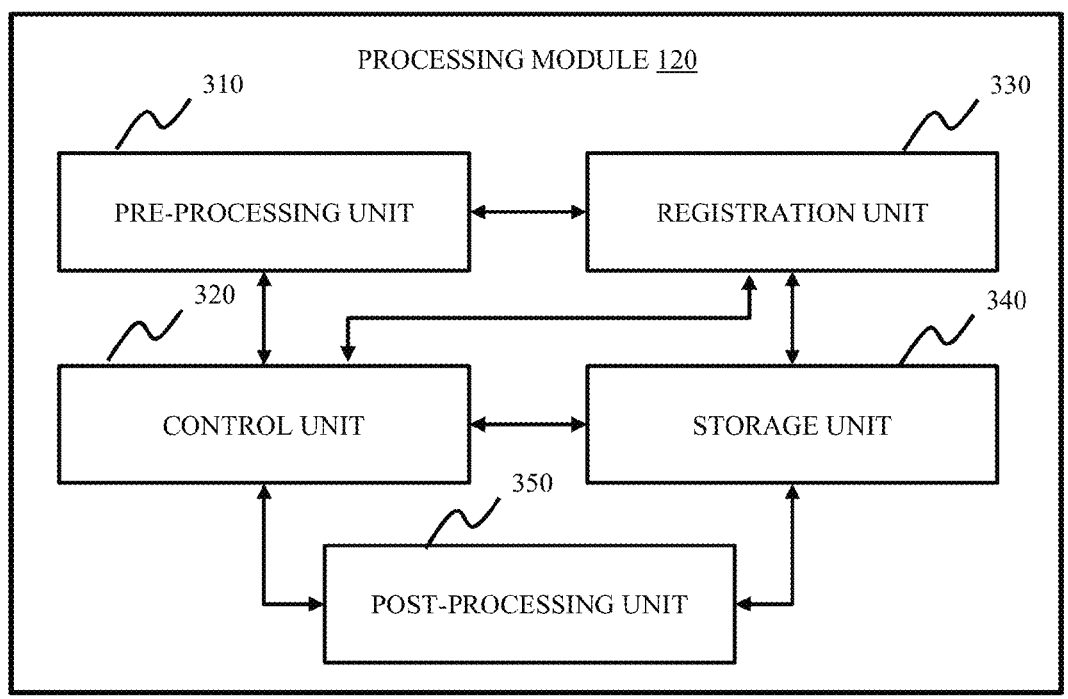
FIG. 3 shows an exemplary diagram of a processing module according to some embodiments of the present disclosure.

FIG. 3 shows an exemplary diagram of a processing module according to some embodiments of the present disclosure. As described in FIG. 3, the processing module may include a pre-processing unit 310, a control unit 320, a registration unit 330, a storage unit 340, and a post-processing unit 350. The communication or data exchange between different units may be via a wired connection or a wireless connection. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), a Wi-Fi, a Wireless a Wide Area Network (WWAN), or the like, or any combination thereof.

The pre-processing unit 310 may acquire and/or send information relating to image processing. The information may be acquired from the control unit 320, the registration unit 330, the storage unit 340, or the post-processing unit 350, or the like, or any combination thereof. The information may include data, such as a number, a text, an image, a voice, a force, a model, an algorithm, a software, a program, or the like, or any combination thereof. For example, the information may include information relating to an object, an operator, an instrument, an instruction, or the like, or any combination thereof, as described elsewhere in the present disclosure.

The control unit 320 may coordinate the execution of image registration. The control unit 320 may obtain and/or forward information relating to an object, an operator, an instrument, and an instruction, etc. from/to the pre-processing unit 310. The control unit 320 may forward at least part of the obtained information to the registration unit 330. For example, various images of an object at different times may be forwarded to the registration unit 330 for processing. The control unit 320 may determine the type of registration to be performed on the images. For example, the control unit 320 may determine the group of spatial transformations, the choice of cost function, and the optimization method. In some embodiments, the control unit 320 may determine a type of coarse registration (see below for detailed description of coarse registration) to be performed. Merely by way of example, the coarse registration may include a group of affine transformations, and the cost function of the normalized mutual information between the images, and the optimization method of the downhill simplex method.

The registration unit 330 may perform the specific image registration on the obtained images. The type of image registration may be selected by the control unit 320. Alternatively, the type of image registration may be selected by the registration unit 330 itself. Based on the selected image registration, the registration unit 330 may choose the corresponding spatial transformation by setting the appropriate mesh size for the images, and choosing the parameters involved in the spatial transformation. The registration unit 330 may determine the type of solver for the selected cost function and the optimization method. The solver may be a matrix solver. In some embodiments, the solver may be an ordinary differential equation (ODE) solver. In some embodiments, the solver may be a partial differential equation (PDE) solver. For instance, the PDE solver may be selected when an elastic model or a fluid model for modeling the offsets of non-rigid meshes is involved.

The storage unit 340 may store information relating to image processing. In some embodiments, the storage unit 340 may store the algorithms related to image registration. For example, algorithms may include algorithms relating to a coarse registration, algorithms related to a fine registration, algorithms related to a super-fine registration.

The storage unit 340 may acquire information from or provide information to other modules. Merely by way of example, some information may be acquired from or output to external resource, such as a floppy disk, a hard disk, a CD-ROM, a wireless terminal, or the like, or any combination thereof.

The storage unit 340 may store information by the way of electric, magnetic, optical energy, or virtual storage resources, etc. The storage module that store information by the way of electric energy may include Random Access Memory (RAM), Read Only Memory (ROM), or the like, or any combination thereof. The storage module that stores information by the way of magnetic energy may include a hard disk, a floppy disk, a magnetic tape, a magnetic core memory, a bubble memory, a USB flash drive, or the like, or any combination thereof. The storage module that store information by the way of optical energy may include CD (Compact Disk), VCD (Video Compact Disk), or the like, or any combination thereof. The storage module that store information by the way of virtual storage resources may include cloud storage, a virtual private network, and/or other virtual storage resources. The method to store information may include sequential storage, link storage, hash storage, index storage, or the like, or any combination thereof.

The post-processing unit 350 may perform post-processing. The post-processing may include disease detection, disease measurement, image display, image storage management, or other 2D and/or 3D post-processing technique or the like, or any combination thereof. Merely by way of example, the images acquired after the image subtraction may contain noise, which may be treated in the post-processing. The display of images may be provided by the post-processing unit 350.

Figure 4:
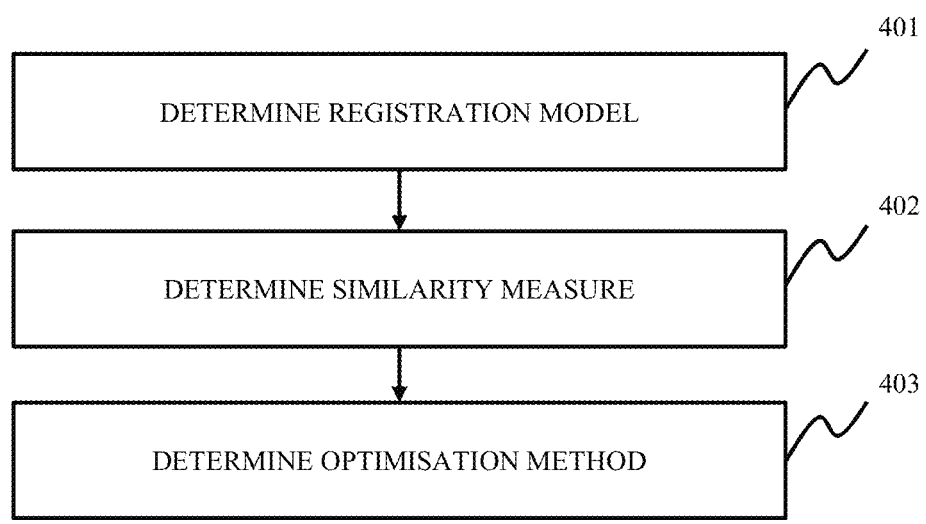
FIG. 4 is an exemplary flowchart illustrating a processing of image registration according to some embodiments of the present disclosure.

It should be noted that the above description of the image processing module is provided for the purposes of illustration, not intended to limit the scope of the present disclosure. For persons having ordinary skills in the art, various variations and modifications may be conducted under the teaching of the present disclosure. However, those variations and modifications may not depart the protecting scope of the present disclosure. For example, the data acquired by the pre-processing unit 310 may be sent to the storage unit 340 and/or the registration unit 330. The control unit 320 may be combined with the storage unit 340 to work as a single operative unit. A subtraction unit may FIG. 4 is an exemplary flowchart illustrating a process for image registration according to some embodiments of the present disclosure. In step 401, a model for image registration may be determined. The model for image registration may designate the group of spatial transformations. For example, the three-dimensional affine transformation may take the following form:

$$\begin{bmatrix} x' \\ y' \\ z' \end{bmatrix} = \begin{bmatrix} a_{11} & a_{12} & a_{13} \\ a_{21} & a_{22} & a_{23} \\ a_{31} & a_{32} & a_{33} \end{bmatrix} \begin{bmatrix} x \\ y \\ z \end{bmatrix} + \begin{bmatrix} t_x \\ t_y \\ t_z \end{bmatrix}, \quad (3)$$

wherein (x', y', z') may be the coordinate of transformed voxels, (x, y, z) may be the coordinate of the voxel before the transformation. The coefficients $a_{11}$, $a_{12}$, $a_{13}$, $a_{21}$, $a_{22}$, $a_{23}$, $a_{31}$, $a_{32}$, $a_{33}$, $t_x$, $t_y$, $t_z$ may be the parameters to be optimized. In another example, the spatial transformation may be based on the B-spline transformation model, where the B-spline function is described by:

$$\begin{bmatrix} x' \\ y' \\ z' \end{bmatrix} = T\left(\begin{bmatrix} x \\ y \\ z \end{bmatrix}\right) = \begin{bmatrix} x \\ y \\ z \end{bmatrix} + \begin{bmatrix} \sum_{l=0}^{3}\sum_{m=0}^{3}\sum_{n=0}^{3} B_l(u)B_m(v)B_n(w)dx_{i+l,j+m,k+n} \\ \sum_{l=0}^{3}\sum_{m=0}^{3}\sum_{n=0}^{3} B_l(u)B_m(v)B_n(w)dy_{i+l,j+m,k+n} \\ \sum_{l=0}^{3}\sum_{m=0}^{3}\sum_{n=0}^{3} B_l(u)B_m(v)B_n(w)dz_{i+l,j+m,k+n} \end{bmatrix}, \quad (4)$$

wherein $$u = x/n_x - \lfloor x/n_x \rfloor, \quad (5)$$

$$v = y/n_y - \lfloor y/n_y \rfloor, \quad (6)$$

$$w = z/n_z - \lfloor z/n_z \rfloor, \quad (7)$$

$$B_0(u) = (1-u)^3/6, \quad (8)$$

$$B_1(u) = (3u^3 - 6u^2 + 4)/6, \quad (9)$$

$$B_2(u) = (-3u^3 + 3u^2 + 3u + 1)/6, \quad (10)$$

$$B_3(u) = u^3/6, \quad (11)$$

and $$i = \lfloor x/n_x \rfloor - 1, j = \lfloor y/n_y \rfloor - 1, k = \lfloor z/n_z \rfloor - 1, \quad (12)$$

may be the indices of a control point, and dx, dy, dz may give the offsets along the X direction, the Y direction, and the Z direction, respectively, of the control points. The set of control points gives the framework of the B-spline transformation, so the movement of the control points along the X direction, the Y direction, and the Z direction, give the parameters to be optimized during the registration.

In some other embodiments, the spatial transformation may be based on modeling of a local deformation field. For example, if the image registration process may be based on image forces and Gaussian regulation of the deformation field, such as a demons method. The transformation model of the demons method may be a local displacement field, i.e., at each and every pixel x, the deformation may be described by a displacement vector u[x], such that T[x]=x+u[x]. The demons method may update the displacement field u iteratively. The displacement field may be updated in each step by adding an increment in the direction of the image force field to the displacement field from the previous step.

In some embodiments, the Demons method may be utilized as the model for the group of spatial transformation. Specifically, the movement of the voxel along the X direction, the Y direction, and the Z direction, respectively, may be determined by the gradient of the gray level of the reference image:

$$u = \frac{2 \times (m-f)(\nabla m + \nabla f)}{(m-f)^2 |\nabla m + \nabla f|^2} \quad (13)$$

Here for a voxel p, f=f(p) is the gray level at p in the reference image, m=m(p) is the gray level at p in the auxiliary image. $\nabla m$ and $\nabla f$ are the gradient of the functions m(p) and f(p), respectively.

In step 402, a similarity measure may be determined. In some embodiments, the similarity measure may be determined based upon the model of spatial transformation. For example, for the spatial transformation given by the affine transformation, the similarity measure may be the mutual information between the images including the reference image and the floating image. In some embodiments, the similarity measure may be normalized mutual information between the images. In some embodiments, the similarity measure may be hybrid normalized mutual information between the images. In some embodiments, the similarity measure may be cross correlation, Mean squared Error, gradient cross-correlation, the difference in the gradient and sum of squared intensity differences between the two images, or the like, or a combination thereof.

In step 403, an optimization method may be determined. The determination of the optimization method may depend upon the spatial transformation and/or the similarity measure. The optimization method considered here may include a Powell method, a downhill simplex method, a gradient descent method, a deepest gradient descending method, a conjugate gradient method, a pseudo-Newton method, a quasi-Newton method, a least-squares and Gauss-Newton method, a Broyden-Fletcher-Goldfarb-Shannon (BFGS) method, a limited-memory Broyden-Fletcher-Goldfarb-Shannon (L-BFGS) method, a simulated annealing method, an ant colony optimization (ACO) method, a genetics algorithm, a Levenberg-Marquardt optimization method, a geometric hashing method, a particle swarm optimization (PSO) method, a firefly algorithm (FA) method, or the like, or a combination thereof.

For example, the L-BFGs method may be implemented as an optimization method. The limited memory BFGS (L-BFGS) method may be substantially similar in its implementation to the BFGS method. The difference may lie in the matrix update method. The BFGS corrections may be stored separately, and when the available storage is used up, the oldest correction may be deleted to make space for the new one. All subsequent iterations may be of this form, i.e. one correction is deleted and a new one inserted.

For another example, the downhill simplex method may be implemented as an optimization method. The downhill simplex method may need only function evaluations, and not calculation of derivatives. In the N-dimensional space, a simplex is a polyhedron with N+1 vertices. N+1 point may be chosen and an initial simplex may be defined in the implementation of the downhill simplex method. The downhill simplex method may update the worst point iteratively by operations of reflection, expansion, one-dimensional contraction, and multiple contractions. For purposes of illustration, reflection may be involved moving the worst point (vertices) of the simplex (where the value of the objective function is the highest) to a point reflected through the remaining N points. If this point is better than the previously best point, then the method may attempt to expand the simplex, and the operation may be called expansion. On the other hand, if the new point is not better than the previous point, then the simplex may be contracted along one dimension from the highest point, and the operation may be called contraction. Moreover, if the new point is worse than the previous points, the simplex may be contracted along all dimensions toward the best point and steps down the valley. By repeating this series of operations, the method may find the optimal solution.

It should be noted that the above description of the image processing module is provided for the purposes of illustration, not intended to limit the scope of the present disclosure. For persons having ordinary skills in the art, various variations and modifications may be conducted under the teaching of the present disclosure. However, those variations and modifications may not depart the protecting scope of the present disclosure.

Figure 5:
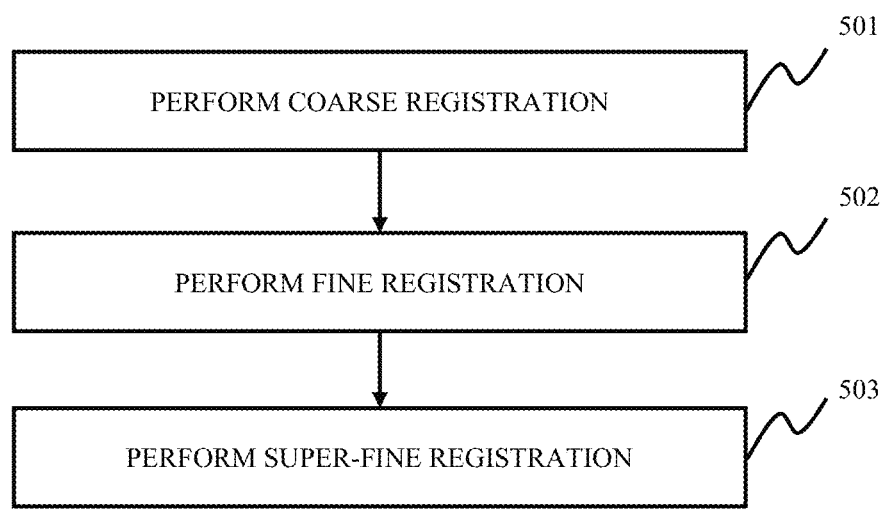
FIG. 5 is an exemplary flowchart illustrating a process for image processing according to some embodiments of the present disclosure.

FIG. 5 is an exemplary flowchart illustrating a process for image processing according to some embodiments of the present disclosure. Two images of an object may be input for a series of image registration to be performed. In step 501, a first registration may be performed on the two images. The first registration may be a coarse registration. The first registration may be based on spatial transformation. One may be referred to as a reference image, and the other one may be referred to as a floating image. The first registration may designate a specific group of spatial transformations to be performed on the floating image. In some embodiments, the group of spatial transformation may be a group of translations. The group of translation may correspond to the case of Equation (3), where the coefficients $a_{12}$, $a_{13}$, $a_{21}$, $a_{23}$, $a_{31}$ and $a_{32}$ may be set to zero, $a_{11}$, $a_{22}$ and $a_{33}$ may be set to 1. In some embodiments, the group of spatial transformations may be a group of rigid motions. The group of rigid motion may correspond to the case of Equation (3), where the matrix $$A = \begin{bmatrix} a_{11} & a_{12} & a_{13} \\ a_{21} & a_{22} & a_{23} \\ a_{31} & a_{32} & a_{33} \end{bmatrix}, \quad (14)$$

may be an orthogonal matrix, i.e., $AA^t = I$, where $$I = \begin{bmatrix} 1 & 0 & 0 \\ 0 & 1 & 0 \\ 0 & 0 & 1 \end{bmatrix}, \quad (15)$$

may be the identity matrix, and $A^t$ may be the transpose of the matrix A. In some embodiments, the group of spatial transformation may be a group of affine transformations.

The selection of the specific spatial transformation to be applied on the floating image may depend the selection of the similarity measure, or referred to as the cost function. To measure the similarity/difference between the images, the cost function may be set by various ways. In some embodiments, the cost function may be given as mutual information. Based on the information theory, mutual information may represent the amount of information that one image may contain about a second image. Mutual information may be maximized by aligning the two images in an optimal way. In some embodiments, the cost function may be given as the mean squared error. In some embodiments, the cost function may be given as the relative entropy. In some embodiments, the cost function may be given as the gradient relative entropy.

An optimization method may be utilized to find a desired spatial transformation for the given cost function. As an example, the group of spatial transformations may be include a group of affine transformations. The cost function may be the mutual information or the normalized mutual information. The optimization method may be the downhill simplex method. As another example, the group of spatial transformation may include a group of rigid motions. The cost function may be the relative entropy. The optimization method may be the Powell method. By performing the coarse registration on the floating image, an intermediate image may be obtained. One or more of the three images, i.e., the reference image, the floating image, and the intermediate image may be provided to step 502.

In step 502, a second registration may be performed on the at least two images input from step 501. The second registration may be performed on the basis of the first registration. The second registration may be a fine registration. One image may be the reference image, and the other may be the intermediate image. In some embodiments, the other image may be the combination of intermediate image and the floating image. The second registration may designate regions of interest (ROI) in the reference image. In some embodiments, the regions of interest may be given as the feature points. A specific group of spatial transformations designating the offsets of the feature points may be chosen. In some embodiments, free-form deformation (FFD) may be used. For example, the $3^{rd}$ order B-spline model may be utilized as the model for the group of spatial transformation. Specifically, the offsets of the voxel along the X direction, the Y direction, and the Z direction may be expressed as the B-spline function of offsets of the 4×4×4 control points adjacent to the voxel according to Equations (4)-(12).

After setting the model for the group of spatial transformations for the second registration, the similarity measure, or referred to as the cost function, may be specified. To measure the similarity/difference between the images, the cost function may be set by various ways. In some embodiments, the cost function may be given as mutual information. Based on information theory, mutual information expresses the amount of information that one image may contain about a second image. Mutual information may be maximized by aligning the two images in an optimal way. In some embodiments, the cost function may be given as the mean squared error. In some embodiments, the cost function may be given as the relative entropy. In some embodiments, the cost function may be given as the gradient relative entropy.

An optimization method may be utilized to find the desired spatial transformation for the given cost function. In some embodiments, the group of spatial transformation may be given as the group of free-form deformation based on the B-spline transformation. The cost function may be the mutual information or the normalized mutual information. The optimization method may be the limited memory Broyden-Fletcher-Goldfarb-Shannon (L-BFGS) method.

In some embodiments, the optimization method may be the Broyden-Fletcher-Goldfarb-Shannon (BFGS) method. By performing the second registration on the intermediate image, an auxiliary image may be obtained. One or all of the three images, i.e. the reference image, intermediate image, and the auxiliary image may be output to step 503.

In step 503, a third registration may be performed on the at least two images input from step 502. The third registration may be performed on the basis of the first registration and/or the second registration. The third registration may be a super-fine registration. One image may be the reference image, and the other may be the auxiliary image. In some embodiments, the other image may be the combination of auxiliary image and the intermediate image or the floating image. The third registration may designate a feature point and/or a structure in the auxiliary image. A feature point may be a point within the image that is indicative of the characteristic of the image. For example, a feature point may be a point with the highest gray level. For another example, a feature point may be a point to designate the positioning of rib(s). A structure may be a formation of feature points. For example, the exhibition of rib(s) within the lung area may be a structure. For another example, the blood vessel may be a structure. In some embodiment, a structure may be formed utilizing partly the feature points. A specific group of spatial transformations designating the offsets of the feature points may be chosen. In some embodiments, a non-rigid registration model based on the gray level may be used. For example, the Demons method may be utilized as the model for the group of spatial transformation. Specifically, the movement of the voxel along the X direction, the Y direction, and the Z direction, respectively, may be determined by the gradient of the gray level of the reference image, which have been described in Equation (15).

After setting the model for the group of spatial transformations for the third registration, the similarity measure, or referred to as the cost function, may be specified. To measure the similarity/difference between the images, the cost function may be set by various ways. In some embodiments, the cost function may be given as mutual information. In some embodiments, the cost function may be given as the mean squared error. In some embodiments, the cost function may be given as the relative entropy. In some embodiments, the cost function may be given as the gradient relative entropy.

An optimization method may be utilized to find the desired spatial transformation for the given cost function. In some embodiments, the group of spatial transformations may be given as the group of free-form deformations based on the non-rigid transformation. The cost function may be the mutual information or the normalized mutual information used to measure the correlevance between the images. The optimization method may be the limited memory Broyden-Fletcher-Goldfarb-Shannon (L-BFGS) method. The limited memory BFGS method is substantially similar in its implementation to the BFGS method. The difference may lie in the matrix update method. The BFGS corrections may be stored separately, and when the available storage is used up, the oldest correction may be deleted to make space for the new one. All subsequent iterations may be of this form, i.e. one correction is deleted and a new one inserted. Alternatively, the optimization method may be the Broyden-Fletcher-Goldfarb-Shannon (BFGS) method.

It should be noted that the flowchart described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure. For example, step 501, step 502 and step 503 may be performed sequentially at an order other than that described above in FIG. 5. Step 501, step 502 and step 503 may be performed concurrently or selectively. Step 501, step 502 and step 503 may be merged into a single step or divided into a number of steps. In addition, one or more other operations may be performed before/after or in performing step 501, step 502 and step 503.

Figure 6:
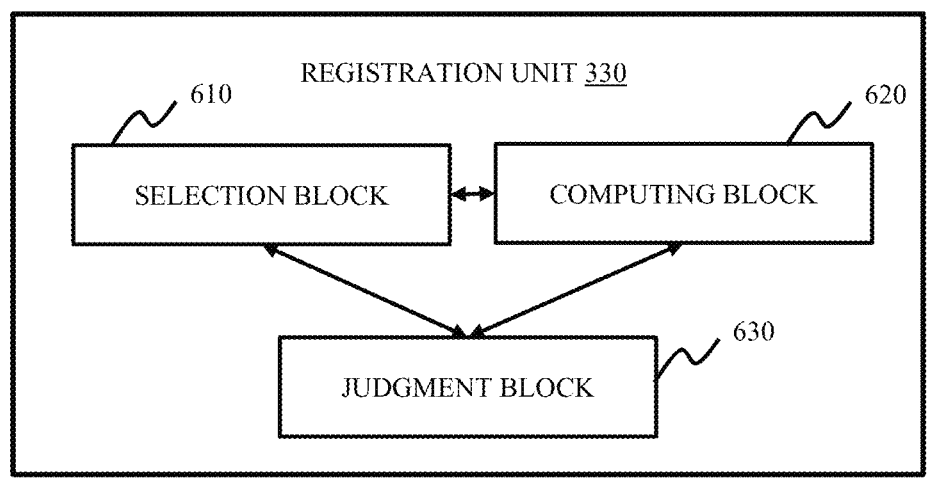
FIG. 6 is an exemplary diagram of an image registration unit according to some embodiments of the present disclosure.

FIG. 6 is an exemplary block diagram of the registration unit 330 according to some embodiments of the present disclosure. The registration unit 330 may include a selection block 610, a computing block 620, and a judgment block 630.

The selection block 610 may determine whether to perform a series of registrations based on the judgment block 630, and which registration may be performed. The selection block 610 may determine which registration model, similarity measure, optimization method to be performed based on information transmitted from the judgment block 630.

The computing block 620 may perform a series of registrations determined by the selection block 610 and/or judgment block 630. For example, the computing block 620 may compute the parameters of similarity measure and the optimization method, such as gray level of voxels, indices of the control points, the coordinate of a transformed voxel, image entropies.

The judgment block 630 may judge the image whether to perform a series of registrations based on the reference image, the desired floating image and the specification of the image processing system. The judgment block 630 may judge whether to compute the parameters of similarity measure, or the optimization method.

It should be noted that the above description of the image processing module is provided for the purposes of illustration, not intended to limit the scope of the present disclosure. For persons having ordinary skills in the art, various variations and modifications may be conducted under the teaching of the present disclosure. However, those variations and modifications may not depart the protecting scope of the present disclosure. For example, the computing block 620 and the judgment block 630 may be incorporated into one block.

Figure 7:
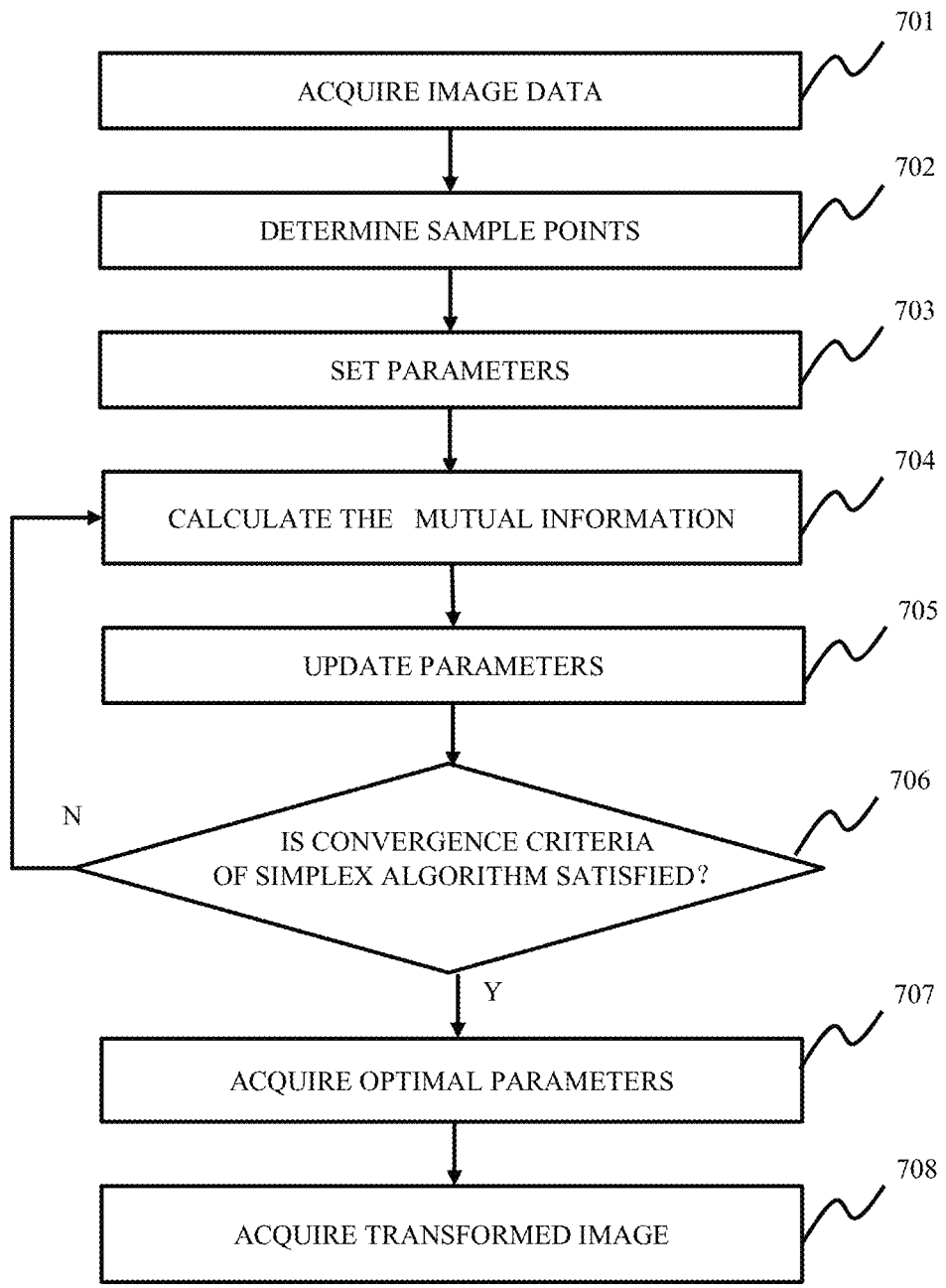
FIG. 7 is an exemplary flowchart illustrating a process for performing a registration according to some embodiments of the present disclosure.

FIG. 7 is an exemplary flowchart illustrating a process for performing a registration according to some embodiments of the present disclosure. The registration may be a coarse registration. At least two images may be obtained in step 701, one image may be the reference image, and the other image may be the floating image. In step 702, one or more feature points located on the reference image may be extracted, also called the sampling points. In step 703, according to the downhill simplex method, the solution space of the initial solution may be set. In an exemplary case in which a 3-dimensional affine transformation is used as the spatial transformation, the number of parameters to be determined may be no less than 13. In step 704, the mutual information for each solution in the solution space may be calculated according to the sampling points and Equation (4) involving the affine transformation. In step 705, the solution space may be updated according to the updating rule of the downhill simplex method and the mutual information of each solution in the solution space. In step 706, the convergence criteria of the downhill simplex method may be checked. If the convergence criteria is satisfied, then the solution obtained may be output as the optimal solution, indicating the optimal affine transformation, into step 707. If the convergence criteria is not satisfied, then the algorithm may go back to step 704. In step 708, the intermediate image may be obtained by performing the optimal affine transformation on the floating image.

It should be noted that the flowchart of performing the algorithm of the coarse registration described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure.

Figure 9:
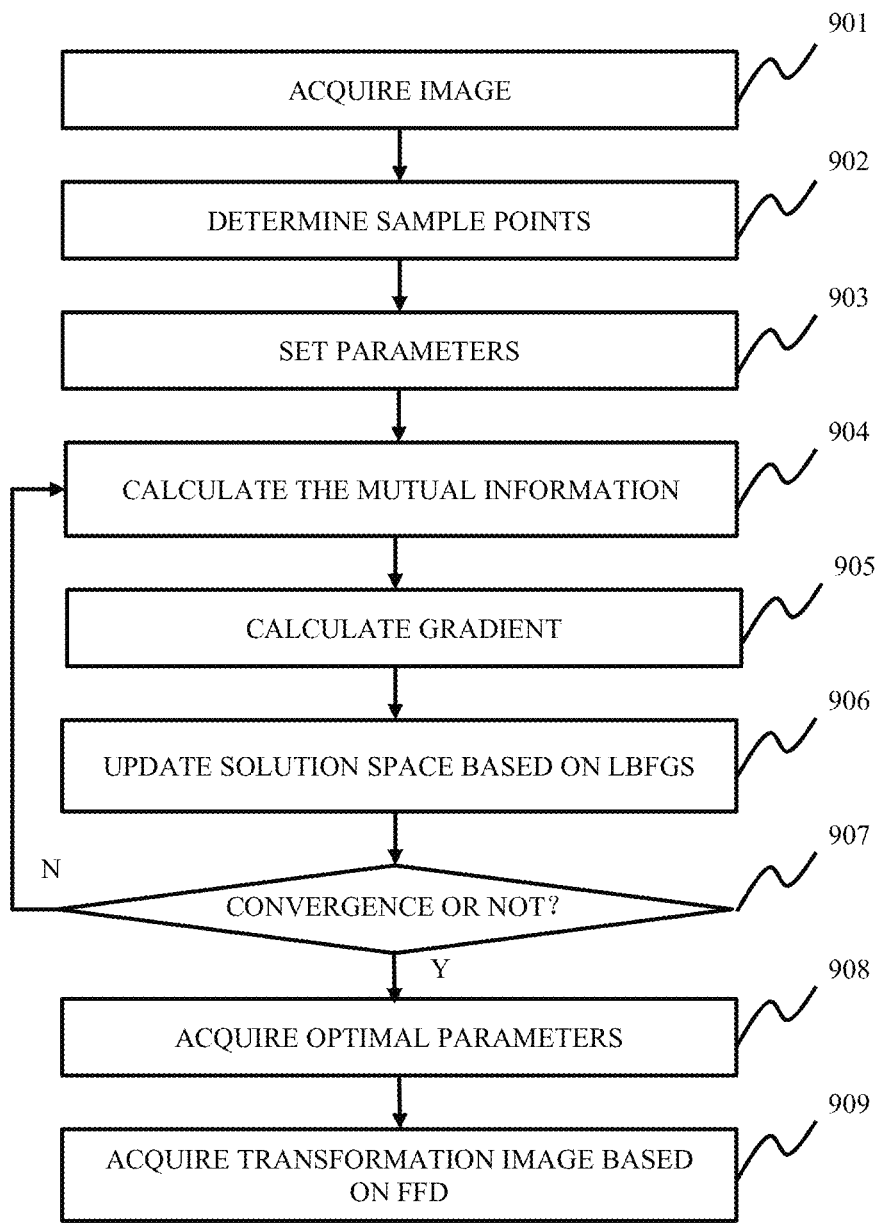
FIG. 9 is an exemplary flowchart illustrating a process for performing a registration according to some embodiments of the present disclosure.

FIG. 9 is an exemplary flowchart illustrating a process for performing a registration according to some embodiments of the present disclosure. The registration may be a fine registration. The registration may be performed on the basis of the registration described elsewhere in the present disclosure, for example, the registration as illustrated in FIG. 7. At least two images may be obtained in step 901, one image may be the reference image, and the other image may be the floating image. For example, the floating image may be the intermediate image obtained from the coarse registration. In step 902, the feature points located on the reference image may be extracted, also called the sampling points. In step 903, according to the L-BFGS method and the B-spline transformation model, the initial solution may be set. In step 904, the mutual information for each solution in the solution space would be calculated according to the sampling points and the model of B-spline transformation, together with the gradient of the mutual information with respect to the optimization variables. In step 905, the solution space would be updated according to the updating rule of the L-BFGS method and/or the mutual information of each solution in the solution space. In step 906, the convergence criteria of the L-BFGS method would be checked. If the convergence criteria is satisfied, then the solution obtained would be output as the optimal solution, indicating the optimal B-spline transformation, into step 907. If the convergence criteria is not satisfied, then the algorithm would go to step 904. In step 908, the auxiliary image may be obtained by performing the optimal B-spline transformation on the floating image.

It should be noted that the flowchart of performing the algorithm of the registration described above in connection with FIG. 9 is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure.

Figure 11:
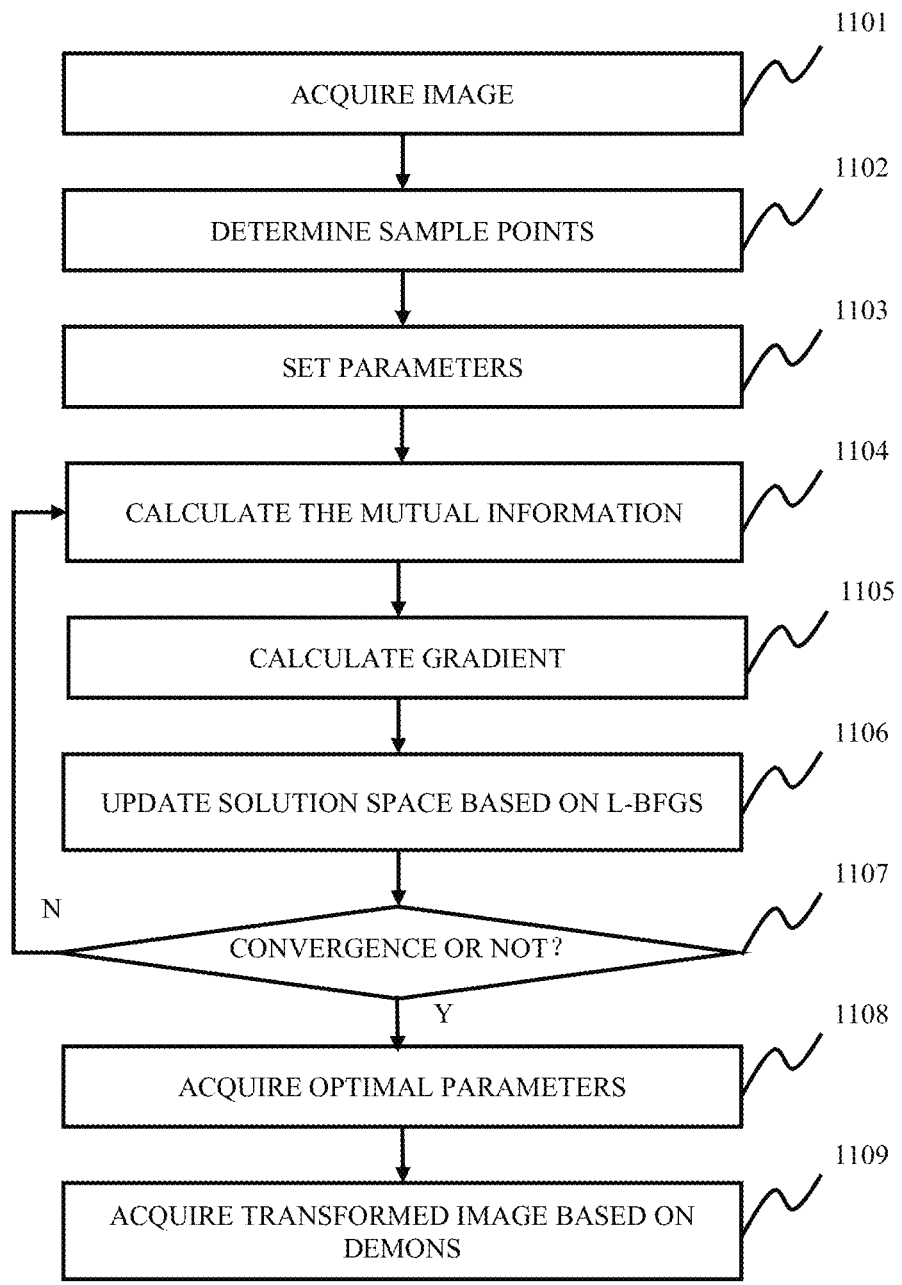
FIG. 11 is an exemplary flowchart illustrating a process for performing a registration according to some embodiments of the present disclosure.

FIG. 11 is an exemplary flowchart illustrating a process for performing a registration according to some embodiments of the present disclosure. The registration may be a super-fine registration. The registration may be performed on the basis of the registration described elsewhere in the present disclosure, for example, the registration as illustrated in FIG. 7 and/or the registration as illustrated in FIG. 9. At least two images may be obtained in step 1101, one image may be the reference image, and the other image may be the floating image. For example, the floating image may be the auxiliary image obtained from the fine registration. In step 1102, the feature points located on the reference image may be extracted, also called the sampling points. The feature points may be chosen to be related to the gray level of the reference image. For example, the feature points may be chosen to be the locations of numerous minor blood vessels in the lung area of a CT image. In step 1103, according to the L-BFGS method and the Demons transformation model, the initial solution may be set. In step 1104, the mutual information for each solution in the solution space would be calculated according to the sampling points and the model of Demons transformation. In step 1105, the gradient of the mutual information with respect to the optimization variables would be calculated. In step 1106, the solution space would be updated according to the updating rule of the L-BFGS method and/or the mutual information of each solution in the solution space. In step 1107, the convergence criteria of the L-BFGS method would be checked. If the convergence criteria is satisfied, then the solution obtained would be output as the optimal solution, singling out the optimal Demons transformation, into step 1108. If the convergence criteria is not satisfied, then the algorithm would go to step 1104. In step 1108, the target image may be obtained by performing the optimal Demons transformation on the floating image.

It should be noted that the flowchart of performing the algorithm of the super-fine registration described above is provided for the purposes of illustration, and not intended to limit the scope of the present disclosure. For persons having ordinary skills in the art, various variations and modifications may be conduct under the teaching of the present disclosure. However, those variations and modifications may not depart from the protecting of the present disclosure.

Figure 13:
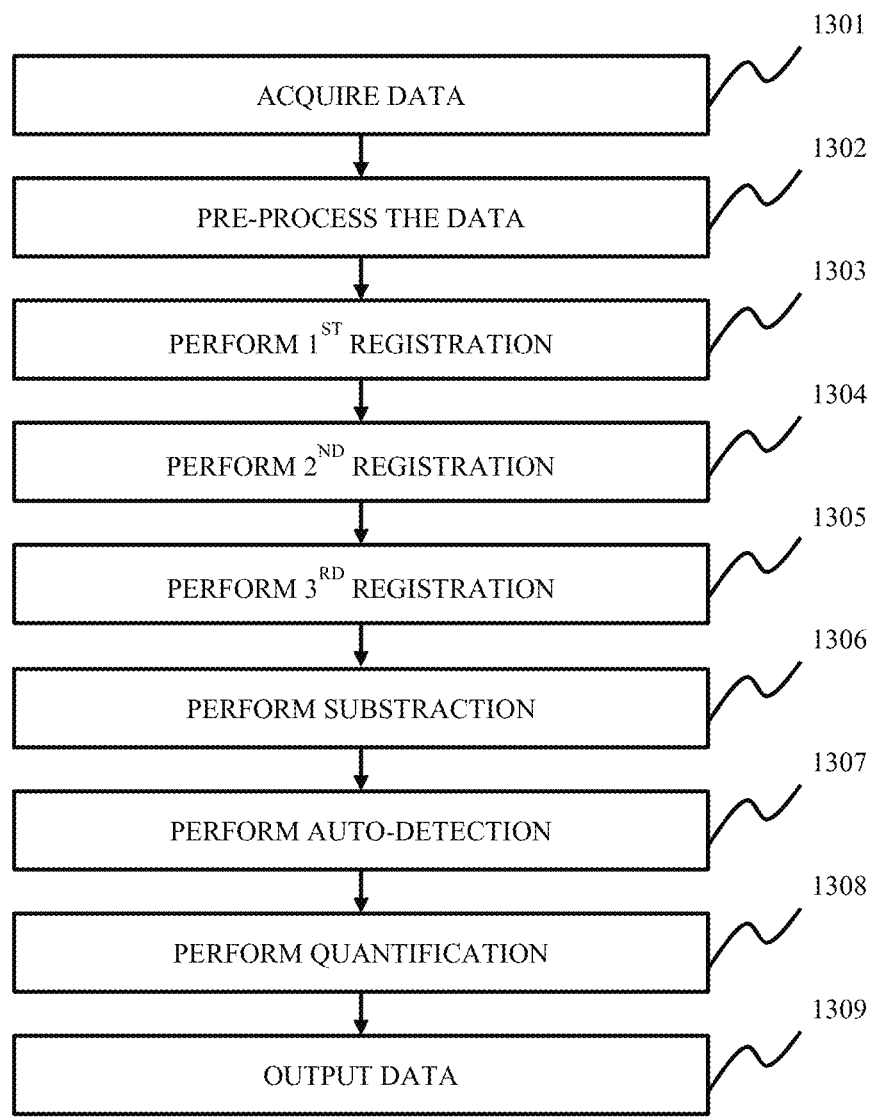
FIG. 13 is an exemplary flowchart illustrating a process for performing a series of registrations according to some embodiments of the present disclosure.

FIG. 13 is an exemplary flowchart illustrating a process for performing a series of registration according to some embodiments of the present disclosure. At least two images may be obtained in step 1301, one image may be the reference image, and the other image may be the floating image. The two images may be two medical images of an object at various stages. For example, the two images may be two CT images of a patient at different times. For another example, the two images may be two DR images of a patient at two stages. In step 1302, the two images may be pre-processed by performing, for example, image normalization, image segmentation, image recognition, image reconstruction, image smoothing, suppressing, weakening and/or removing a detail, a mutation, a noise, or the like, or any combination thereof. In step 1303, a first registration of two images may be implemented. For example, a coarse registration may be implemented on the two images to generate an intermediate image. The three images, i.e. the reference image, the floating image, and the intermediate image may be output into step 1304. In step 1304, a second registration may be implemented on the three images. For example, a fine registration may be implemented on the reference image and the intermediate image to produce an auxiliary image as the output image. In step 1305, a third registration on the reference image and the auxiliary image may be implemented to produce the target image. In step 1306, a temporal subtraction image may be obtained by subtracting the target image from the reference image, illustrating the possible locations of new lesion, and/or the possible locations of diminished lesion. In step 1307, an auto-detection may be implemented on the temporal subtraction image to single out the region of interests for further processing. In step 1308, quantification of the data from the images generated during the whole procedure may be produced, such as the volume of the lesion, the density of the region of interest, the object information about the patient, the instrument information and the instruction information. In some embodiments, the volume corresponding to each pixel or voxel in the lesion area (or the region of interest), of a medical image may be obtained, either in an empirical or a statistical way. The total volume of the lesion may then be obtained by multiplying the number of pixels or voxels in the lesion area, with the specific volume corresponding to each pixel or voxel. In some embodiments, the density of the lesion area (or the region of interest) in each pixel or voxel of a medical image may be obtained, either in an empirical or a statistical way. The mass of the lesion area (or the region of interest) corresponding to each pixel or voxel may then be calculated. The total mass of the lesion area (or the region of interest) may then be obtained by summing up the mass in all pixels or voxels in the lesion area. In step 1309 the images together with the relevant data may be output to a display device.

It should be noted that the flowchart of performing the algorithm of the super-fine registration described above is provided for the purposes of illustration, and not intended to limit the scope of the present disclosure. For example, the size and location of the lesions of one object may be obtained using the procedure as illustrated in FIG. 13 at different stages, either in an automatic or a manual way. The difference of the size of the lesion, and/or the rate of change of the size of lesion may be derived taking into account of time when the images of the object were generated. In some embodiments, the reference image, the floating image, and the subtraction image may be displayed on the same display device in a row. In some embodiments, the reference image, the floating image, and/or the subtraction image may be displayed on the same display device in a column. For persons having ordinary skills in the art, various variations and modifications may be conduct under the teaching of the present disclosure. However, those variations and modifications may not depart from the protecting of the present disclosure.

EXAMPLES

The following examples are provided for illustration purposes, and not intended to limit the scope of the present disclosure.

Example 1

Figure 8A:
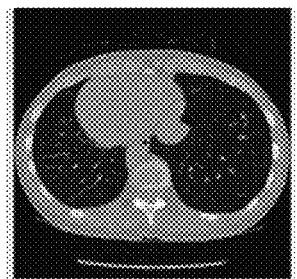
FIG. 8A through FIG. 8C demonstrate some exemplary images obtained by performing the registration as illustrated in FIG. 7.
Figure 8B:
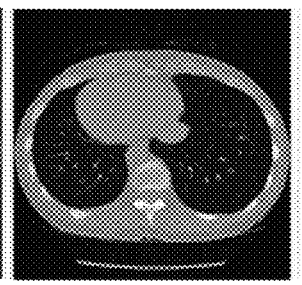
Figure 8C:
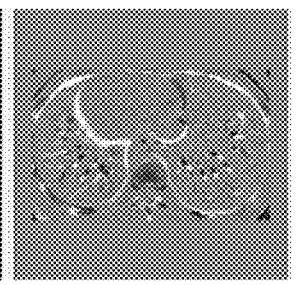

FIG. 8A through FIG. 8C demonstrate some exemplary figures after the coarse registration as illustrated in FIG. 7. FIG. 8A is a reference image, and FIG. 8B is a floating image, whereas FIG. 8C gives the temporal subtraction image between the reference image and an intermediate image. The intermediate image was obtained from the operation of the coarse registration between the reference image and the floating image.

Example 2

Figure 10A:
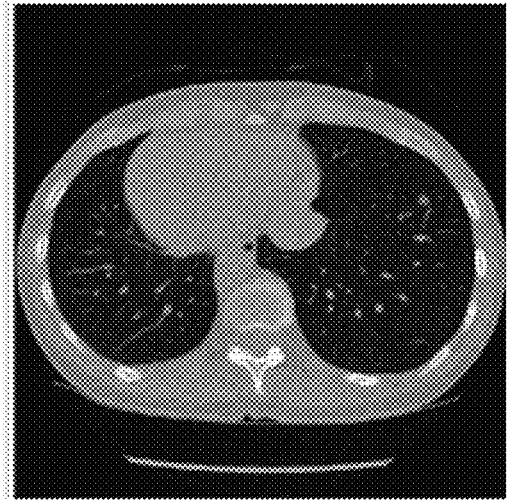
FIG. 10A through FIG. 10D demonstrate some exemplary images obtained by performing the registration as illustrated in FIG. 9.
Figure 10B:
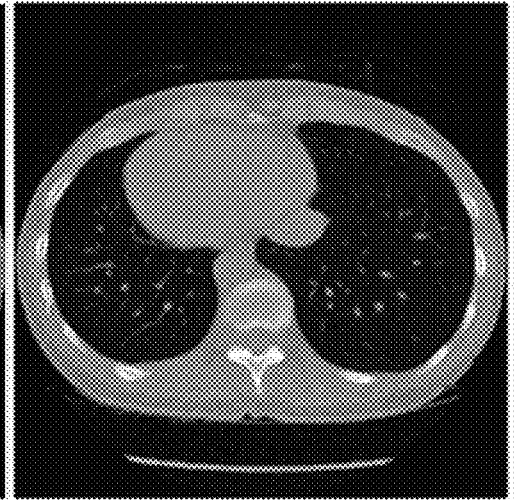
Figure 10C:
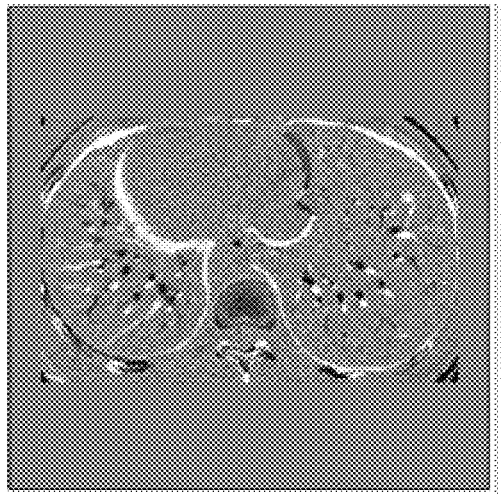
Figure 10D:
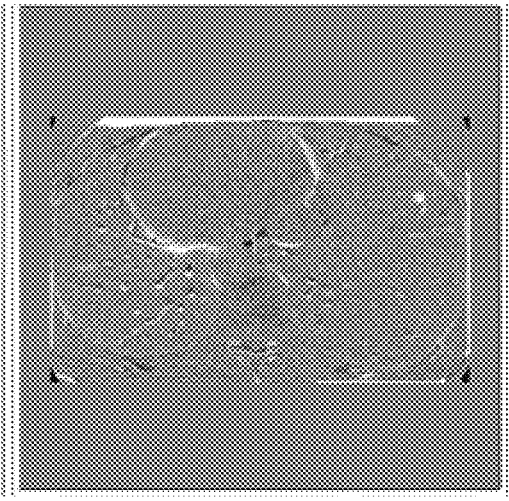

FIG. 10A through FIG. 10D demonstrate some exemplary figures after the fine registration as illustrated in FIG. 9. FIG. 10A is a reference image, FIG. 10B is a floating image, and FIG. 10C gives the temporal subtraction image between the reference image and an intermediate image. The intermediate image was obtained from the operation of the coarse registration between the reference image and the floating image. There are still many shadowy areas exhibiting blood vessels in the lung area. FIG. 10D gives a temporal subtraction image between the reference image and an auxiliary image. The auxiliary image was obtained from the operation of the fine registration between the reference image and the intermediate image.

Example 3

Figures 12A, 12B:
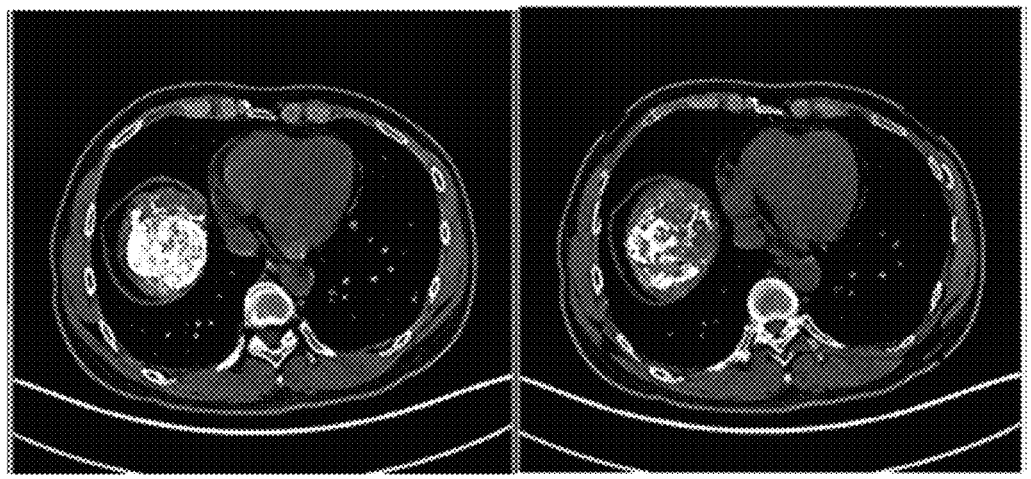
FIG. 12A through FIG. 12D demonstrate some exemplary images obtained by performing the registration as illustrated in FIG. 11.
Figures 12C, 12D:
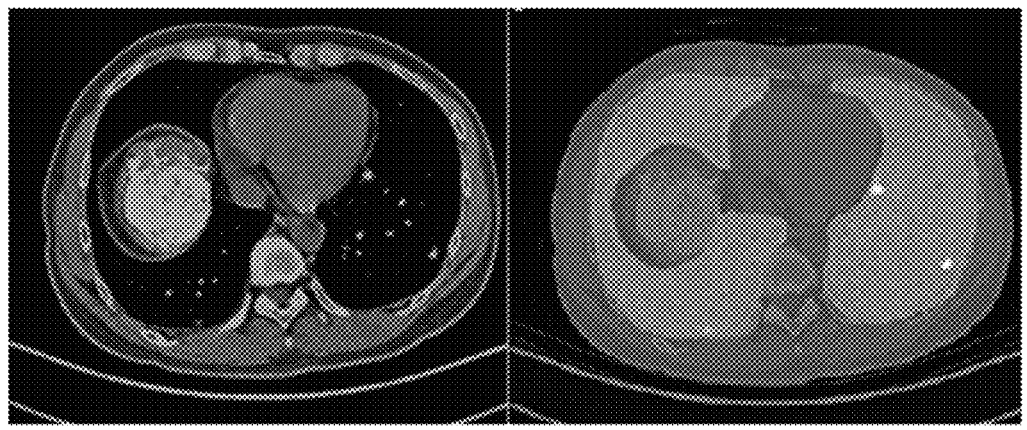

FIG. 12A through FIG. 12D demonstrate some exemplary figures after the super-fine registration as illustrated in FIG. 11. FIG. 12A is a reference image, FIG. 12B is a floating image, and FIG. 12D gives a temporal subtraction image between the reference image and a target image (or referred to as an auxiliary image). The target image was obtained from the operation of the super-fine registration on the floating image. There are but a few prominent shadowy areas in the lung area. FIG. 12C gives a fused image between the reference image and the temporal subtraction image. Note the red dots in FIG. 12C that designate the corresponding feature points in FIG. 12 D, which is indicative of the change of the lesion.

Example 4

Figure 14A:
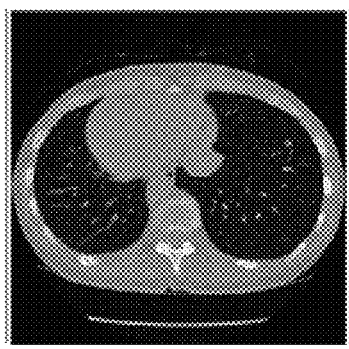
FIGS. 14A-14F illustrate six CT images that were generated based on image registration according to some embodiments of the present disclosure.
Figure 14B:
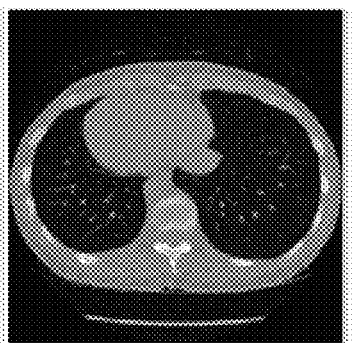
Figure 14C:
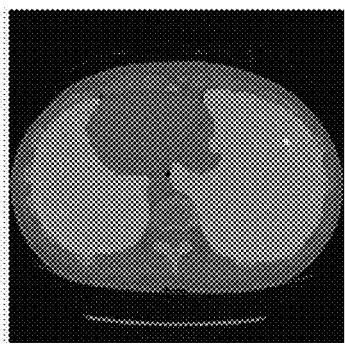
Figure 14D:
Figure 14E:
Figure 14F:

FIGS. 14A-14F illustrate six CT images that were generated based on image registration according to an algorithm for performing a series of registration as illustrated in FIG. 13. FIGS. 14A, 14B and FIGS. 14D, 14E are two sets of reference images and floating images, respectively, wherein FIG. 14C and FIG. 14F are the temporal subtraction images generated based on the various image registration or a combination thereof as described in the present disclosure.

Example 5

Figure 15A:
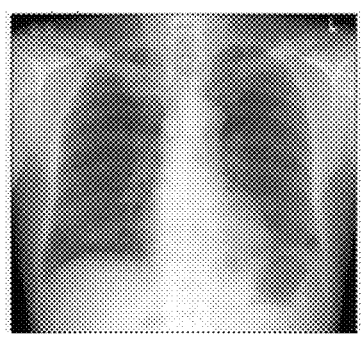
FIGS. 15A-15F illustrate six X-ray images that were generated based on image registration according to some embodiments of the present disclosure.
Figure 15B:
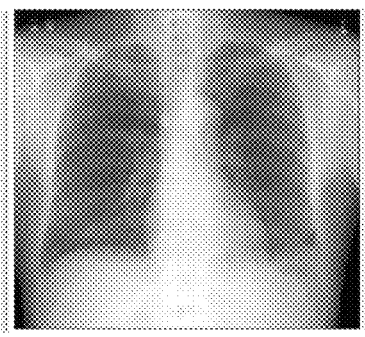
Figure 15C:
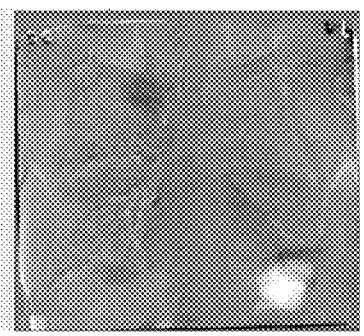
Figure 15D:
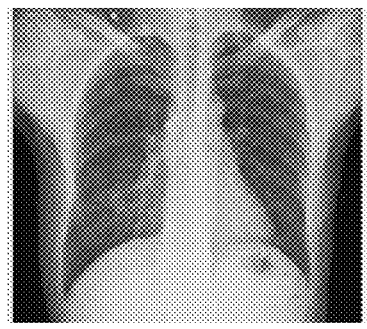
Figure 15E:
Figure 15F:
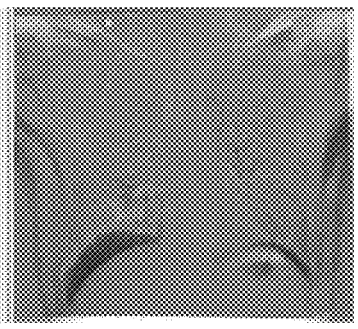

FIGS. 15A-15F illustrate six X-ray images that were generated based on image registration according to an algorithm for performing a series of registration as illustrated in FIG. 13. FIGS. 15A, 15B and FIGS. 15D, 15E are two sets of reference images and floating images, respectively, wherein FIG. 15C and FIG. 15F are the temporal subtraction images generated based on the various image registration or a combination thereof as described in the present disclosure.

Example 6

Fifty-nine CT images and 232 DR images were processed utilizing the image registration described herein. To evaluate the quality of subtraction images, objective ratings by five radiologists and five physicists were utilized independently. A four-point rating scale below was then generated based on the objective ratings:

1 Bad: Most ribs (or Vessels) are not well registered;

2 Acceptable: Most ribs (or Vessels) are well registered, with some minor mis-registration error;

3 Good: Most ribs (or Vessels) are almost completely registered with some very minor mis-registrations; and 4 Excellent: All ribs (or Vessels) are perfectly registered.

The rating for each case was determined in one of the four categories above based on the average (or the majority) of the ratings provided by multiple observers. The test result on the total 291 data images may be classified into four categories: "excellent," "good," "acceptable," and "bad" as above. Two hundred twenty-nine results are excellent, 56 results are good, 2 results are acceptable, and 4 results are bad. Approximately 97.9% results are excellent or good.

As will be also appreciated, the above described method embodiments may take the form of computer or controller implemented processes and apparatuses for practicing those processes. The disclosure can also be embodied in the form of computer program code containing instructions embodied in tangible media, such as floppy diskettes, CD-ROMs, hard drives, or any other computer-readable storage medium, wherein, when the computer program code is loaded into and executed by a computer or controller, the computer becomes an apparatus for practicing the invention. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, may be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein. Variations on those preferred embodiments will become apparent to those of ordinary skill in the art upon reading the foregoing description. It is contemplated that skilled artisans may employ such variations as appropriate, and the application may be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method comprising:
designating a first image of an object as a reference image, the reference image comprising at least a reference feature point and a reference structure;
obtaining a second image of the object, the second image comprising a feature point and a structure, the feature point corresponding to the reference feature point of the reference image, the structure corresponding to the reference structure of the reference image;
performing a first registration of the second image to obtain a first registered image, the first registration comprising an affine transformation, the first registered image comprising the feature point and the structure;
performing a second registration of the first registered image to obtain a second registered image, the second registration comprising aligning the structure in the first registered image with the reference structure in the reference image, the second registered image comprising the feature point;
performing a third registration of the second registered image to obtain a third registered image, the third registration comprising aligning the feature point in the second registered image with the reference feature point in the reference image; and
subtracting the third registered image from the reference image to obtain a subtraction image comprising the feature point or the structure.

2. The method of claim 1, wherein the second registration is based on the free form deformation model transformation.

3. The method of claim 1, wherein the third registration is based on the Demons model transformation.

4. The method of claim 1, wherein the first registration is based on an optimization of either mutual information or a mean squared error.

5. The method of claim 4, wherein the first registration comprises a downhill simplex method.

6. The method of claim 1, wherein the second registration is based on an optimization of either mutual information or a mean squared error.

7. The method of claim 6, wherein the second registration comprises an L-BFGS method.

8. The method of claim 1, wherein the third registration is based on an optimization of either mutual information or a mean squared error.

9. The method of claim 8, wherein the third registration comprises an L-BFGS method.

10. The method of claim 1, wherein the first image and the second image are taken at different times.

11. The method of claim 1, wherein the first image, the second image, and the subtraction image are displayed on a same display device.

12. The method of claim 1, wherein the reference feature point in the first image and the feature point in the second image are displayed in the subtraction image.

13. The method of claim 1, wherein the feature point and the structure in the subtraction image are fused with the reference image for showing the change of the feature point or the structure in the subtraction image over the reference feature point or the reference structure.

14. The method of claim 1 further comprising: identifying, in the subtraction image, a region of interest including the feature point in the second image, and quantifying a pathological change of the feature point in the region of interest.

15. A non-transitory computer-readable medium containing instructions that, when executed by a processor, cause the processor to perform operations comprising:
designating a first image of an object as a reference image, the reference image comprising at least a reference feature point and a reference structure;
obtaining a second image of the object, the second image comprising a feature point and a structure, the feature point corresponding to the reference feature point of the reference image, the structure corresponding to the reference structure of the reference image;
performing a first registration of the second image to obtain a first registered image, the first registration comprising an affine transformation, the first registered image comprising the feature point and the structure;
performing a second registration of the first registered image to obtain a second registered image, the second registration comprising aligning the structure in the first registered image with the reference structure in the reference image, the second registered image comprising the feature point;
performing a third registration of the second registered image to obtain a third registered image, the third registration comprising aligning the feature point in the second registered image with the reference feature point in the reference image; and
subtracting the third registered image from the reference image to obtain a subtraction image.

16. A system of image processing, comprising:
an image processing module configured to:
designate a first image of an object as a reference image, the reference image comprising at least a reference feature point and a reference structure;
obtain a second image of the object, the second image comprising a feature point and a structure, the feature point corresponding to the reference feature point of the reference image, the structure corresponding to the reference structure of the reference image;
perform a first registration of the second image to obtain a first registered image, the first registration comprising an affine transformation, the first registered image comprising the feature point and the structure;
perform a second registration of the first registered image to obtain a second registered image, the second registration comprising aligning the structure in the first registered image with the reference structure in the reference image, the second registered image comprising the feature point;
perform a third registration of the second registered image to obtain a third registered image, the third registration comprising aligning the feature point in the second registered image with the reference feature point in the reference image; and
subtract the third registered image from the reference image to obtain a subtraction image comprising the feature point or the structure.

17. The system of claim 16, wherein the image processing module comprises a post-processing unit to perform lesion detection and lesion measurement.

18. The system of claim 16, wherein the image processing module comprises a control unit configured to control the performance of a series of registrations.

19. The system of claim 16, wherein the image processing module comprises an image display unit for displaying at least one of the first reference image, the second reference image, the third reference image, or the subtraction image.

20. The system of claim 16, wherein the image processing module is further configured to:
identify, in the subtraction image, a region of interest including the feature point in the second image; and
quantify a pathological change of the feature point in the region of interest.

* * * * *